(12) United States Patent
Fukushima et al.

(10) Patent No.: US 7,915,442 B2
(45) Date of Patent: Mar. 29, 2011

(54) PROCESS FOR PRODUCING ALIPHATIC NITRILES

(75) Inventors: Tetsuaki Fukushima, Wakayama (JP); Michio Terasaka, Wakayama (JP)

(73) Assignee: Kao Corporation, Tokyo (JP)

( * ) Notice: Subject to any disclaimer, the term of this patent is extended or adjusted under 35 U.S.C. 154(b) by 333 days.

(21) Appl. No.: 12/281,152

(22) PCT Filed: Feb. 27, 2007

(86) PCT No.: PCT/JP2007/054132
§ 371 (c)(1), (2), (4) Date: Aug. 29, 2008

(87) PCT Pub. No.: WO2007/102448
PCT Pub. Date: Sep. 13, 2007

(65) Prior Publication Data
US 2009/0054677 A1    Feb. 26, 2009

(30) Foreign Application Priority Data
Mar. 8, 2006 (JP) .................................. 2006-062455

(51) Int. Cl.
*C07C 253/00* (2006.01)
(52) U.S. Cl. ........................................................ 558/311
(58) Field of Classification Search .................... 558/311
See application file for complete search history.

(56) References Cited

U.S. PATENT DOCUMENTS

| | | | |
|---|---|---|---|
| 4,166,805 A | 9/1979 | Jowett | |
| 4,234,509 A | 11/1980 | Billenstein et al. | |
| 6,005,134 A * | 12/1999 | Terasaka et al. | 558/311 |
| 7,259,274 B2 * | 8/2007 | Terasaka et al. | 558/311 |

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

The present invention relates to a process for producing an aliphatic nitrile, including the step of reacting at least one compound selected from the group consisting of an aliphatic monocarboxylic acid, an aliphatic dicarboxylic acid and alkyl esters of these acids containing an alkyl group having 1 to 5 carbon atoms, with ammonia in the presence of a compound of at least one metal selected from the group consisting of zinc, cobalt, titanium and aluminum, and a sulfonic acid compound! and a process for producing an aliphatic amine, including the step of subjecting the aliphatic nitrile produced by the above process to hydrogenation reaction in the presence of a hydrogenation catalyst. There are provided an industrially advantageous process for producing an aliphatic nitrile with a high reactivity; and a process for producing an aliphatic amine using the aliphatic nitrile as a raw material.

6 Claims, No Drawings

PROCESS FOR PRODUCING ALIPHATIC NITRILES

FIELD OF THE INVENTION

The present invention relates to a process for producing aliphatic nitrites, and a process for producing aliphatic amines from the aliphatic nitrites produced by the process.

BACKGROUND OF THE INVENTION

As a process for producing aliphatic nitrites, there are generally known industrial processes in which an aliphatic carboxylic acid or a derivative thereof is reacted with ammonia. The methods used in the reaction for producing the aliphatic nitrites are generally classified into a gas phase method and a liquid phase method. In the reaction conducted by the liquid phase method, there has been extensively used such a process in which the carboxylic acid or the derivative thereof is dissolved under heating, and then ammonia is blown into the obtained solution to react these compounds with each other in the presence of a catalyst by a batch method or a continuous method.

In the case where the reaction is conducted by such a liquid phase method, there are known processes for producing the aliphatic nitrites by using a catalyst such as, for example, zinc oxide or an iron compound. Also, there are disclosed the process for producing aliphatic nitriles using a composite oxide composed of titanium oxide and an oxide of at least one element selected from the group consisting of silicon, niobium, zirconium, tantalum, gallium and germanium as a catalyst (refer to JP 2000-80069A and JP 2000-80070A), the process for producing aliphatic nitrites using titanium oxide supported on solid silica as a catalyst (refer to JP 2005-89361A), etc.

However, in recent years, there is a demand for conducting these conventional production processes with a still higher reactivity.

SUMMARY OF THE INVENTION

The present invention relates to the following aspects [1] and [2]:

[1] A process for producing an aliphatic nitrile, including the step of reacting at least one compound selected from the group consisting of an aliphatic monocarboxylic acid, an aliphatic dicarboxylic acid and alkyl esters of these acids containing an alkyl group having 1 to 5 carbon atoms, with ammonia in the presence of a compound of at least one metal selected from the group consisting of zinc, cobalt, titanium and aluminum, and a sulfonic acid compound; and

[2] a process for producing an aliphatic amine, including the steps of:

(1) producing an aliphatic nitrile by the process as defined in the above aspect [1]; and (2) subjecting the obtained aliphatic nitrile to hydrogenation reaction in the presence of a hydrogenation catalyst.

DETAILED DESCRIPTION OF THE INVENTION

The present invention relates to an industrially advantageous process for producing an aliphatic nitrile with a high reactivity, and a process for producing an aliphatic amine by using the aliphatic nitrile as a raw material.

<Process for Producing Aliphatic Nitrile>

In the process for producing an aliphatic nitrile according to the present invention, at least one compound selected from the group consisting of an aliphatic monocarboxylic acid, an aliphatic dicarboxylic acid and alkyl esters of these acids containing an alkyl group having 1 to 5 carbon atoms is reacted with ammonia in the presence of a compound of at least one metal selected from the group consisting of zinc, cobalt, titanium and aluminum, and a sulfonic acid compound.

In the present invention, the compound of at least one metal selected from the group consisting of zinc, cobalt, titanium and aluminum is selectively used in view of preventing counter ions from hindering the reaction conducted in the production process of the present invention, and decreasing a yield of the aimed aliphatic nitrile. Examples of the preferred metal compound include an oxide, a hydroxide, a carbonate, a nitrate, a sulfate, an alkoxide, a carboxylate and an acetylacetonate of these metals. Among these metal compounds, especially preferred are an oxide, a hydroxide, a carboxylate and an alkoxide of the metals. Also, as the at least one metal selected from the group consisting of zinc, cobalt, titanium and aluminum, in view of reducing the costs for the catalyst used in the production process, preferred are zinc, aluminum and titanium, and more preferred are zinc and aluminum.

These metal compounds may be used alone or in combination of any two or more thereof.

Examples of the sulfonic acid compound used in the present invention include an aryl sulfonic acid which may be substituted with an alkyl group, and an alkyl sulfonic acid.

Specific examples of the aryl sulfonic acid which may be substituted with an alkyl group include benzenesulfonic acid, benzenesulfonic acids which are mono-, di- or tri-alkylated with a linear or branched alkyl group having 1 to 22 carbon atoms, and naphthalene monosulfonic acids or polysulfonic acids. Among these aryl sulfonic acids, in view of lowering an amount of the sulfonic acid compound charged owing to a smaller molecular weight thereof as well as decreasing residues upon purifying the resultant product by distillation, preferred are monoalkyl benzenesulfonic acids containing a linear alkyl group.

Examples of the alkyl sulfonic acid include alkyl monosulfonic acids and alkyl disulfonic acids containing a linear or branched alkyl group having 1 to 22 carbon atoms. In view of a good catalytic activity, preferred are linear alkyl monosulfonic acids, and more preferred are alkyl sulfonic acids containing an alkyl chain in which a part or whole of hydrogen atoms are substituted with a halogen atom. Specific examples of the halogen atom include fluorine, chlorine, bromine and iodine. Among these halogen atoms, preferred is fluorine.

Specific examples of the sulfonic acid compound include benzenesulfonic acid, toluenesulfonic acid, p-ethyl benzenesulfonic acid, n-propyl benzenesulfonic acid, n-butyl benzenesulfonic acid, n-hexyl benzenesulfonic acid, octyl benzenesulfonic acid, n-dodecyl benzenesulfonic acid, cetyl benzenesulfonic acid, octadecyl benzenesulfonic acid, triisobutyl benzenesulfonic acid, n-butyl naphthalenesulfonic acid, n-octanesulfonic acid, n-dodecyl sulfonic acid, octadecyl sulfonic acid, trifluoromethanesulfonic acid, 1-perfluorobutanesulfonic acid, 1-perfluorohexanesulfonic acid and 1-perfluorooctanesulfonic acid. Among these sulfonic acid compounds, in view of a good catalytic activity, preferred are toluenesulfonic acid, p-ethyl benzenesulfonic acid, n-propyl benzenesulfonic acid, n-butyl benzenesulfonic acid, n-hexyl benzenesulfonic acid, trifluoromethanesulfonic acid, 1-perfluorobutanesulfonic acid and 1-perfluorohexanesulfonic acid.

In the present invention, at least one compound selected from the group consisting of an aliphatic monocarboxylic acid, an aliphatic dicarboxylic acid and alkyl esters of these acids containing an alkyl group having 1 to 5 carbon atoms is reacted with ammonia in the presence of the above metal compound and the sulfonic acid compound. Examples of the aliphatic monocarboxylic acid, the aliphatic dicarboxylic acid and the alkyl esters of these acids (containing an alkyl group having 1 to 5 carbon atoms) used in the present invention include linear or branched aliphatic monocarboxylic acids having 6 to 22 carbon atoms, linear or branched aliphatic dicarboxylic acids having 6 to 22 carbon atoms, and alkyl esters of these acids containing an alkyl group having 1 to 5 carbon atoms. Among these compounds, preferred are aliphatic monocarboxylic acids having 8 to 22 carbon atoms and alkyl esters of these acids containing an alkyl group having 1 to 5 carbon atoms. Also, the above aliphatic monocarboxylic acid, aliphatic dicarboxylic acid or alkyl esters of these acids usable in the present invention may be either saturated or unsaturated.

The number of carbon atoms of the alkyl group contained in the above alkyl esters preferably lies within the above specified range in view of a usefulness of the resultant nitriles. Specific examples of the alkyl group having 1 to 5 carbon atoms include methyl, ethyl, propyl and isopropyl. Among these alkyl groups, from the above viewpoint, especially preferred is methyl. These aliphatic monocarboxylic acid, aliphatic dicarboxylic acids and alkyl esters of these acids containing an alkyl group having 1 to 5 carbon atoms may be used alone or in combination of any two or more thereof.

Specific examples of the aliphatic monocarboxylic acid and the aliphatic dicarboxylic acid include caproic acid, caprylic acid, capric acid, lauric acid, myristic acid, palmitic acid, stearic acid, arachic acid, behenic acid, dimethyl octanoic acid, butylheptyl nonanoic acid, hexenoic acid, octenoic acid, decenoic acid, dodecenoic acid, tetradecenoic acid, hexadecenoic acid, octadecenoic acid, eicosenoic acid, docosenoic acid, adipic acid, azelaic acid, sebacic acid, decamethylenedicarboxylic acid, hexadecamethylenedicarboxylic acid and octadecamethylenedicarboxylic acid. Among these aliphatic monocarboxylic and dicarboxylic acids, in view of a good reactivity and a good selectivity, preferred are the aliphatic monocarboxylic acids.

Specific examples of the alkyl esters of the aliphatic monocarboxylic and dicarboxylic acids which contain an alkyl group having 1 to 5 carbon atoms include methyl esters, ethyl esters, propyl esters and isopropyl esters of these aliphatic monocarboxylic and dicarboxylic acids. Among these alkyl esters, from the above viewpoint, preferred are methyl esters and ethyl esters of the aliphatic monocarboxylic and dicarboxylic acids.

The ammonia to be reacted with the at least one compound selected from the group consisting of an aliphatic monocarboxylic acid, an aliphatic dicarboxylic acid and alkyl esters of these acids containing an alkyl group having 1 to 5 carbon atoms is used in an amount of preferably 1 to 300 mol, more preferably 2 to 100 mol and even more preferably 2 to 50 mol per 1 mol of the aliphatic monocarboxylic acid, the aliphatic dicarboxylic acid or the alkyl ester in view of a good reactivity and a good selectivity.

The compound of at least one metal selected from the group consisting of zinc, cobalt, titanium and aluminum as a catalyst is used in an amount of preferably 0.01 to 20% by mass, more preferably 0.05 to 15% by mass and even more preferably 0.05 to 10% by mass on the basis of the aliphatic monocarboxylic acid, the aliphatic dicarboxylic acid or the alkyl ester in view of a good catalytic activity and a high yield of the aimed nitrile.

The sulfonic acid compound as a catalyst is used in an amount of preferably not less than 0.01 equivalent but less than 1 equivalent, more preferably from 0.05 to 0.6 equivalent and even more preferably from 0.1 to 0.3 equivalent per one equivalent of the metal in view of a good catalytic activity. In particular, when at least one compound selected from the group consisting of an unsaturated aliphatic monocarboxylic acid, an unsaturated aliphatic dicarboxylic acid and alkyl esters of these acids is reacted with ammonia, the amount of the sulfonic acid compound preferably lies within the above specified range in view of a good catalytic reactivity and a high yield of the aimed nitrile separated from a reaction product mixture by distillation, etc.

The process for producing the aliphatic nitrile according to the present invention may be carried out by any of a suspension type batch method, a semi-batch method, a continuous method and a fixed bed flow method.

When the production process is conducted by a batch method or a semi-batch method, there may be used such a process in which after dissolving the aliphatic monocarboxylic acid, the aliphatic dicarboxylic acid and/or the alkyl ester of these acids, charging a predetermined amount of the catalyst into a reaction vessel and fully purging the reaction vessel with nitrogen, the contents of the reaction vessel are heated to a predetermined reaction temperature, and then an ammonia gas is flowed into the reaction vessel.

When the production process is conducted by a continuous method or a fixed bed flow method, there may be used such a process in which after charging the catalyst to a reaction system and heating the system to the reaction temperature, a solution in which the aliphatic monocarboxylic acid, the aliphatic dicarboxylic acid or the alkyl ester of these acids is dissolved, is flowed into the system together with ammonia.

The production process may be carried out under normal pressure, and is preferably carried out under a slightly pressurized state. The reaction temperature is preferably from 180 to 400° C., more preferably from 230 to 370° C. and even more preferably from 250 to 360° C. in view of a good reactivity and a high selectivity.

Also, the method of separating and purifying the aimed aliphatic nitrile from the reaction solution obtained in the above reaction step is not particularly limited, and the separation and purification procedure may be conducted by any suitable known methods such as, for example, concentration, distillation, extraction, crystallization, re-crystallization, column chromatography and combination of these methods.

<Process for Producing Aliphatic Amine>

In the process for producing an aliphatic amine according to the present invention, the aliphatic nitrile is produced according to the above production process (step (1)), and then the resultant aliphatic nitrile is subjected to hydrogenation reaction in the presence of a hydrogenation catalyst (step (2)).

As the hydrogenation catalyst used in the step (2), there may be suitably used any known hydrogenation catalysts such as, for example, cobalt-based catalysts, nickel-based catalysts, copper-based catalysts and noble metal-based catalysts. Among these catalysts, in view of a good reactivity and a high selectivity, preferred are catalysts containing nickel, cobalt, and/or ruthenium as a main component, and more preferred are Raney type catalysts, and the catalysts supported on a porous metal oxide such as silica, alumina, silica-alumina, diatomaceous earth and activated carbon. In addition, the hydrogenation catalyst may also contain other metals such as aluminum, zinc and silicon. Further, these hydrogenation catalysts may contain a metal selected from the group consisting of chromium, iron, cobalt, manganese, tungsten and molybdenum as a reaction accelerator.

The hydrogenation catalyst may be used in the form of a complete solid catalyst. Alternatively, the hydrogenation catalyst may also be used in the form of a supported solid catalyst, for example, obtained by supporting nickel, cobalt, ruthenium, etc., on a carrier such as aluminum oxide, titanium oxide, zirconium oxide and magnesia/alumina.

In the present invention, the hydrogenation catalyst may be used in an amount of preferably 0.05 to 5% by mass and more preferably 0.1 to 3% by mass on the basis of the aliphatic nitrile used in view of a good reactivity and a high selectivity.

The hydrogenation reaction pressure is preferably from 0.1 to 5 MPaG, more preferably from 0.5 to 4 MPaG and still more preferably from 0.8 to 3 MPaG in terms of a hydrogen pressure. The hydrogenation reaction temperature is preferably from 50 to 200° C., more preferably from 80 to 170° C. and even more preferably from 100 to 140° C. in view of a good reactivity and a high selectivity. During the hydrogenation reaction, the reaction temperature is preferably raised continuously or stepwise.

According to the present invention, the aliphatic nitrile can be produced with a high reactivity. When using the thus produced aliphatic nitrile as a raw material, the aliphatic amine can be produced at low costs.

The aliphatic nitrile produced by the process of the present invention can be suitably used for production of the aliphatic amine. Also, the aliphatic amine is an important intermediate material for products used in domestic or industrial application fields. For example, the aliphatic amine can be suitably used in extensive applications such as softeners for fiber products, antistatic agents, additives for gasoline, shampoos, rinses, disinfectants and detergents.

The present invention is described in more detail by referring to the following examples. However, it should be noted that these examples are only illustrative and not intended to limit the invention thereto.

EXAMPLE 1

A four-necked separable flask equipped with a stirrer, a gas feed pipe, a thermometer and a dehydrator was charged with 500 g of a hardened tallow fatty acid (main components: C14; 3.8%, C16; 28.7%, C18; 61.9%), 0.5 g of zinc oxide (0.10% by mass based on fatty acid) and 0.59 g of p-toluenesulfonic acid monohydrate (0.12% by mass based on fatty acid; 0.25 equivalent based on zinc), and the contents of the flask were stirred at 500 rpm. The obtained reaction solution was heated to 300° C. and the temperature was kept constant at 300° C. to conduct the reaction thereof, while flowing an ammonia gas therethrough at a rate of 1000 mL/min from the point at which a temperature of the reaction solution reached 210° C. until completion of the reaction.

After the elapse of 3 h from initiation of flowing the ammonia gas through the reaction solution, the obtained reaction product was subjected to gas chromatography [gas chromatograph: "HEWLETT PACKARD Series 6890"; column: "HP-5" available from J & W Scientific Inc. (column inner diameter x length: 0.25 mm×60 m); the column temperature was kept at 120° C. as an initial value for 2 min, and then raised to 300° C., a temperature rise rate of 8° C./min, followed by maintaining at 300° C. for 5.5 min; detector: FID detector] to analyze a composition thereof and measure a yield of a hardened tallow nitrile produced. The results are shown in Table 1. Meanwhile, the "reaction terminating time" used hereinafter means a time taken from initiation of flowing the ammonia gas through the reaction solution until an amount of an aliphatic amide produced reached a level below a detection limit as measured by the above gas chromatography.

COMPARATIVE EXAMPLE 1

The same procedure as in Example 1 was repeated except that the reaction was conducted using zinc oxide solely without adding p-toluenesulfonic acid monohydrate thereto, thereby producing a reaction product and analyzing a composition of the thus obtained reaction product. The results are shown in Table 1.

EXAMPLES 2 TO 4

The same procedure as in Example 1 was repeated except for using 500 g of a distilled tallow fatty acid (main components: C16; 27.1%, C16:1; 2.4%, C18; 21.3%, C18:1; 36.9%, C18:2; 2.3%) in place of the hardened tallow fatty acid, using cobalt stearate, aluminum hydroxide and tetraisopropoxy titanium in such amounts as shown in Table 1, respectively, in place of zinc oxide, and further changing the amount of p-toluenesulfonic acid monohydrate used, as shown in Table 1, thereby producing a reaction product and analyzing a composition of the thus obtained reaction product. The results are shown in Table 1.

COMPARATIVE EXAMPLES 2 TO 4

The same procedure as in Comparative Example 1 was repeated except for using 500 g of a distilled tallow fatty acid in place of the hardened tallow fatty acid, and using cobalt stearate, aluminum hydroxide and tetraisopropoxy titanium in such amounts as shown in Table 1, respectively, in place of zinc oxide, thereby producing a reaction product and analyzing a composition of the thus obtained reaction product. The results are shown in Table 1.

TABLE 1

| | Metal compound | | Sulfonic acid compound* | | Equivalent (based on metal) |
|---|---|---|---|---|---|
| | Kind | Amount* (mass %) | Kind | Amount* (mass %) | |
| Example 1 | Zinc oxide | 0.10 | p-toluenesulfonic acid | 0.12 | 0.25 |
| Comparative Example 1 | Zinc oxide | 0.10 | p-toluenesulfonic acid | — | — |
| Example 2 | Cobalt stearate | 0.77 | p-toluenesulfonic acid | 0.12 | 0.25 |
| Comparative Example 2 | Cobalt stearate | 0.77 | p-toluenesulfonic acid | — | — |
| Example 3 | Aluminum hydroxide | 0.10 | p-toluenesulfonic acid | 0.12 | 0.17 |
| Comparative Example 3 | Aluminum hydroxide | 0.10 | p-toluenesulfonic acid | — | — |
| Example 4 | Tetra-isopropoxy titanium | 0.36 | p-toluenesulfonic acid | 0.12 | 0.13 |
| Comparative Example 4 | Tetra-isopropoxy titanium | 0.36 | p-toluenesulfonic acid | — | — |

| | Yield of nitrile after 3 h (%) | Reaction terminating time (h) |
|---|---|---|
| Example 1 | 99.4 | 3.4 |
| Comparative Example 1 | 97.6 | 4.4 |
| Example 2 | 98.1 | 3.4 |
| Comparative Example 2 | 96.1 | 4.5 |
| Example 3 | 89.5 | 7.2 |
| Comparative Example 3 | 81.1 | — |
| Example 4 | 95.4 | 3.7 |

TABLE 1-continued

| Comparative Example 4 | 91.6 | 4.3 |

Note:
*Percent by mass on the basis of aliphatic monocarboxylic acid, aliphatic dicarboxylic acid or alkyl esters of these acids.

EXAMPLE 5

The same procedure as in Example 1 was repeated except for using 500 g of a distilled tallow fatty acid in place of the hardened tallow fatty acid, and using 0.15 g (0.03% by mass based on fatty acid; 0.08 equivalent based on zinc) of trifluoromethanesulfonic acid in place of 0.59 g of p-toluenesulfonic acid monohydrate, thereby producing a reaction product and analyzing a composition of the obtained reaction product. As a result, it was confirmed that the yield of the nitrile produced after the elapse of 3 h from initiation of flowing an ammonia gas through the reaction solution was 98.6%, and the time taken from the initiation of flowing an ammonia gas until the amount of the aliphatic amide produced reached a level below a detection limit as measured by gas chromatography (reaction terminating time) was 3.6 h.

COMPARATIVE EXAMPLE 5

The same procedure as in Comparative Example 1 was repeated except for using 500 g of a distilled tallow fatty acid in place of the hardened tallow fatty acid, thereby producing a reaction product and analyzing a composition of the obtained reaction product. As a result, it was confirmed that the yield of the nitrile produced after the elapse of 3 h from initiation of flowing an ammonia gas through the reaction solution was 97.0%, and the time taken from the initiation of flowing an ammonia gas until the amount of the aliphatic amide produced reached a level below a detection limit as measured by gas chromatography (reaction terminating time) was 4.1 h.

EXAMPLE 6

The same procedure as in Example 1 was repeated except for changing the amount of p-toluenesulfonic acid monohydrate used from 0.59 g to 1.17 g (0.23% by mass based on fatty acid; 0.50 equivalent based on zinc), thereby producing a reaction product and analyzing a composition of the obtained reaction product. As a result, it was confirmed that the yield of the nitrile produced after the elapse of 3 h from initiation of flowing an ammonia gas through the reaction solution was 99.5%, and the time taken from the initiation of flowing an ammonia gas until the amount of the aliphatic amide produced reached a level below a detection limit as measured by gas chromatography (reaction terminating time) was 3.1 h.

Further, the reaction product thus obtained by the above reaction which contained the catalyst was charged into a glass container equipped with a thermometer, a capillary tube, a cooling pipe, a fraction receiving container and a vacuum gage, and after the pressure within the reaction system was reduced to 0.53 kPa, the temperature was gradually raised to conduct distillation of the reaction product until the bottom temperature reached 240° C. in maximum. As a result, it was confirmed that the yield of the oleonitrile produced by distillation was 95.0%.

EXAMPLE 7

The same procedure as in Example 1 was repeated except for using 500 g of methyl stearate (purity: 98.5%) in place of the hardened tallow fatty acid, thereby producing a reaction product and analyzing a composition of the obtained reaction product. As a result, it was confirmed that the yield of the stearonitrile produced after the elapse of 4 h from initiation of flowing an ammonia gas through the reaction solution was 87.9%, and the time taken from the initiation of flowing an ammonia gas until the amount of the aliphatic amide produced reached a level below a detection limit as measured by gas chromatography (reaction terminating time) was 6.3 h.

COMPARATIVE EXAMPLE 6

The same procedure as in Comparative Example 1 was repeated except for using 500 g of methyl stearate (purity: 98.5%) in place of the hardened tallow fatty acid, thereby producing a reaction product and analyzing a composition of the obtained reaction product. As a result, it was confirmed that the yield of the stearonitrile produced after the elapse of 4 h from initiation of flowing an ammonia gas through the reaction solution was 81.1%, and the time taken from the initiation of flowing an ammonia gas until the amount of the aliphatic amide produced reached a level below a detection limit as measured by gas chromatography (reaction terminating time) was 7.1 h.

EXAMPLE 8

A four-necked separable flask equipped with a stirrer, a gas feed pipe, a thermometer and a dehydrator was charged with 500 g of a coconut oil fatty acid (main components: C8: 5.8%, C10; 6.0%, C12; 49.1%, C14; 19.3%, C16; 9.6%, C18:1; 5.8%), 1.0 g of zinc oxide (0.20% by mass based on fatty acid) and 1.17 g of p-toluenesulfonic acid monohydrate (0.23% by mass based on fatty acid; 0.25 equivalent based on zinc), and the contents of the flask were stirred at 500 rpm. The obtained reaction solution was heated to 280° C. and the temperature was kept constant at 280° C. to conduct the reaction thereof, while flowing an ammonia gas therethrough at a rate of 1300 mL/min from the point at which a temperature of the reaction solution reached 210° C. until completion of the reaction.

As a result of analyzing the reaction product obtained after the elapse of 3 h from initiation of flowing an ammonia gas through the reaction solution in the same manner as in Example 1, it was confirmed that the yield of the nitrile produced was 96.3%, and the time taken from the initiation of flowing an ammonia gas until the amount of the aliphatic amide produced reached a level below a detection limit as measured by gas chromatography (reaction terminating time) was 3.8 h.

COMPARATIVE EXAMPLE 7

The same procedure as in Example 8 was repeated except that the reaction was conducted using 1.0 g of zinc oxide solely without adding p-toluenesulfonic acid monohydrate thereto, thereby producing a reaction product and analyzing a composition of the obtained reaction product. As a result, it was confirmed that the yield of the nitrile produced after the elapse of 3 h from initiation of flowing an ammonia gas through the reaction solution was 77.3%, and the time taken from the initiation of flowing an ammonia gas until the amount of the aliphatic amide produced reached a level below a detection limit as measured by gas chromatography (reaction terminating time) was 5.9 h.

EXAMPLE 9

The same procedure as in Example 1 was repeated except for using 500 g of oleic acid "LUNAC O-A" available from Kao Corp., in place of the hardened tallow fatty acid, and changing the amount of p-toluenesulfonic acid monohydrate used from 0.59 g to 2.34 g (0.47% by mass based on fatty acid; 1.00 equivalent based on zinc), thereby producing a reaction product and analyzing a composition of the obtained reaction product. As a result, it was confirmed that the time taken from initiation of flowing an ammonia gas through the reaction solution until the amount of the aliphatic amide produced reached a level below a detection limit as measured by gas chromatography (reaction terminating time) was 2.9 h.

Further, the reaction product thus obtained by the above reaction was charged into a glass container equipped with a thermometer, a capillary tube, a cooling pipe, a fraction receiving container and a vacuum gage, and after the pressure within the reaction system was reduced to 0.53 kPa, the temperature was gradually raised to conduct distillation of the reaction product until any fraction was no longer distilled off (bottom temperature: 240° C. in maximum). The yield of the oleonitrile produced by distillation is shown in Table 2.

EXAMPLES 10 AND 11 AND COMPARATIVE EXAMPLE 8

The same procedure as in Example 9 was repeated except that the amount of p-toluenesulfonic acid monohydrate used was changed as shown in Table 1. The reaction terminating time was measured by the same method as in Example 9. Further, the obtained reaction product was subjected to the same distillation procedure as in Example 9. The results are shown in Table 2.

TABLE 2

| | Metal compound | | Sulfonic acid compound* | | |
|---|---|---|---|---|---|
| | Kind | Amount* (mass %) | Kind | Amount* (mass %) | Equivalent (based on metal) |
| Example 9 | Zinc oxide | 0.10 | p-toluenesulfonic acid | 0.47 | 1.00 |
| Example 10 | Zinc oxide | 0.10 | p-toluenesulfonic acid | 0.23 | 0.50 |
| Example 11 | Zinc oxide | 0.10 | p-toluenesulfonic acid | 0.06 | 0.13 |
| Comparative Example 8 | Zinc oxide | 0.10 | p-toluenesulfonic acid | — | — |

| | Reaction terminating time (h) | Yield of nitrile by distillation (%) |
|---|---|---|
| Example 9 | 2.9 | 92.0 |
| Example 10 | 2.9 | 93.9 |
| Example 11 | 3.2 | 95.0 |
| Comparative Example 8 | 4.0 | 95.2 |

Note:
*Percent by mass on the basis of aliphatic monocarboxylic acid, aliphatic dicarboxylic acid or alkyl esters of these acids.

EXAMPLE 12

The reaction product obtained in Example 1 was distilled to remove the zinc compound and then 400 g of the distilled reaction product, 1.4 g of a Raney nickel catalyst, 0.8 g of 48% NaOH and 8.8 g of ion-exchanged water were charged into an autoclave. Thereafter, a gas phase portion of the autoclave was replaced with hydrogen to adjust a hydrogen pressure therein to 1.9 MPaG, and then the contents of the autoclave were heated to 135° C. and reacted with each other. The reaction was terminated at the time at which no absorption of hydrogen occurred, and further the resultant reaction mixture was aged for 30 min. The absorption of hydrogen smoothly proceeded and completed after 2.2 h. After completion of the reaction and aging, the obtained reaction product was withdrawn from the reaction vessel to remove the catalyst therefrom, and then purified by distillation under a pressure of 0.27 kPa at 220° C., thereby obtaining a hardened tallow amine with a yield of 96%.

The invention claimed is:

1. A process for producing an aliphatic nitrile, comprising the step of reacting at least one compound selected from the group consisting of an aliphatic monocarboxylic acid, an aliphatic dicarboxylic acid and alkyl esters of these acids containing an alkyl group having 1 to 5 carbon atoms, with ammonia in the presence of a compound having at least one metal selected from the group consisting of zinc, cobalt, titanium and aluminum, and a sulfonic acid compound.

2. The process according to claim 1, wherein the sulfonic acid compound is used in an amount of not less than 0.01 equivalent but less than 1 equivalent per one equivalent of the at least one metal selected from the group consisting of zinc, cobalt, titanium and aluminum.

3. The process according to claim 1, wherein the compound having at least one metal selected from the group consisting of zinc, cobalt, titanium and aluminum is used in an amount of 0.01 to 20% by mass on the basis of the at least one compound selected from the group consisting of an aliphatic monocarboxylic acid, an aliphatic dicarboxylic acid and alkyl esters of these acids containing an alkyl group having 1 to 5 carbon atoms.

4. The process according to claim 1, wherein the sulfonic acid compound is an aryl sulfonic acid which may be substituted with an alkyl group or an alkyl sulfonic acid.

5. The process according to claim 1, wherein the compound having at least one metal selected from the group consisting of zinc, cobalt, titanium and aluminum is an oxide, a hydroxide, a carboxylate or an alkoxide of the metal.

6. The process according to claim 1, wherein the at least one compound selected from the group consisting of an aliphatic monocarboxylic acid, an aliphatic dicarboxylic acid and alkyl esters of these acids containing an alkyl group having 1 to 5 carbon atoms is reacted with ammonia at a temperature of 180 to 400° C.

* * * * *